United States Patent
Hussein et al.

(10) Patent No.: US 11,918,421 B2
(45) Date of Patent: Mar. 5, 2024

(54) LOUPES PROTECTION SHIELDS USEFUL IN DENTAL APPLICATIONS

(71) Applicant: University of Florida Research Foundation, Inc., Gainesville, FL (US)

(72) Inventors: Hind Sattar Hussein, Lakewood Ranch, FL (US); Nader Farhan Abdulhameed, Lakewood Ranch, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 717 days.

(21) Appl. No.: 17/084,168

(22) Filed: Oct. 29, 2020

(65) Prior Publication Data

US 2021/0137630 A1     May 13, 2021

Related U.S. Application Data

(60) Provisional application No. 62/931,993, filed on Nov. 7, 2019.

(51) Int. Cl.
| | | |
|---|---|---|
| *G02B 7/00* | (2021.01) | |
| *A61B 90/00* | (2016.01) | |
| *A61C 13/15* | (2006.01) | |

(52) U.S. Cl.
CPC .............. *A61B 90/04* (2016.02); *G02B 7/006* (2013.01); *A61B 2090/0454* (2016.02); *A61B 2090/049* (2016.02); *A61C 19/003* (2013.01)

(58) Field of Classification Search
CPC ............ A61B 90/04; A61B 2090/0454; A61B 2090/049; A61C 19/003; A61C 1/08; G02B 7/006; G02B 5/208; G02B 5/223
See application file for complete search history.

(56) References Cited

U.S. PATENT DOCUMENTS

| | | | |
|---|---|---|---|
| 5,182,588 A | | 1/1993 | Maurer et al. |
| 6,102,556 A | * | 8/2000 | Lieberman ............. G03B 17/12 362/16 |
| 6,371,612 B2 | | 4/2002 | Barrows |
| 7,813,787 B2 | * | 10/2010 | de Josselin de Jong .................... A61B 1/0607 600/478 |
| 8,786,689 B1 | * | 7/2014 | Liu .......................... A61B 1/24 348/68 |
| 9,052,455 B2 | | 6/2015 | Chang |
| 2010/0210951 A1 | * | 8/2010 | Rahman ............... A61B 5/0071 600/476 |
| 2010/0305436 A1 | * | 12/2010 | Chen ................... A61B 5/0059 600/431 |
| 2021/0038339 A1 | * | 2/2021 | Yu .......................... A61B 90/30 |

* cited by examiner

*Primary Examiner* — Mustak Choudhury
(74) *Attorney, Agent, or Firm* — Thomas | Horstemeyer, LLP

(57) ABSTRACT

Described herein are loupes shields. The shields can be easily attached to the loupes. The loupes shield is composed of a single filter that blocks harmful light. Additionally, the loupes shield includes a connector that permits the loupes shield to be attached to the loupes lens or housing that holds the loupes lens. The loupes shields described are useful in applications where it is desirable to protect the user from being exposed to damaging light. The loupes shields are useful in dental applications such as, for example, dental restorations, where light cure is required to cure the resin applied to a tooth during a dental restoration.

9 Claims, 1 Drawing Sheet

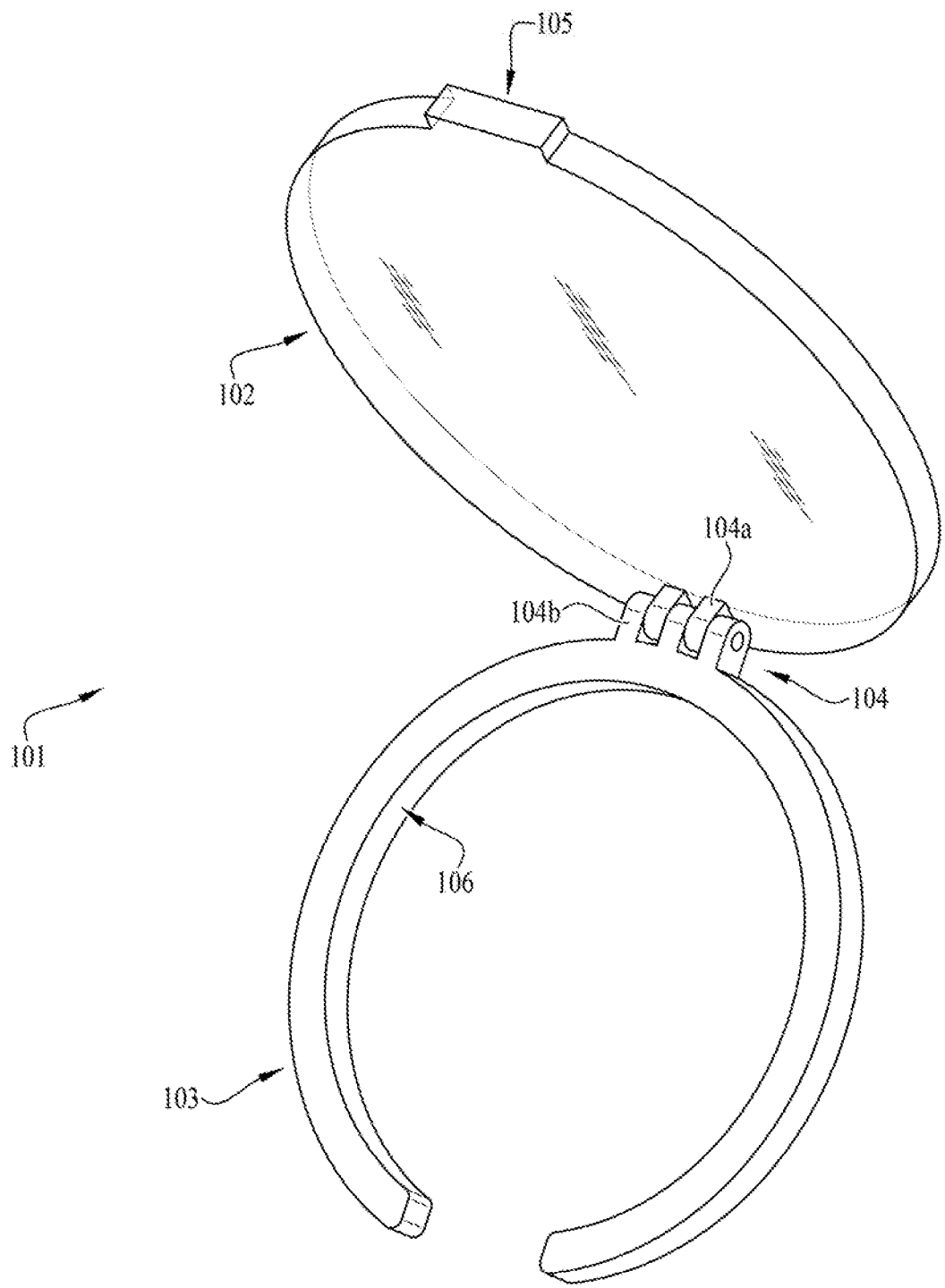

LOUPES PROTECTION SHIELDS USEFUL IN DENTAL APPLICATIONS

CROSS REFERENCE TO RELATED APPLICATIONS

This application claims the benefit of U.S. Provisional Patent Application Ser. No. 62/931,993 filed on Nov. 7, 2019, the entire contents of which are hereby incorporated by reference.

BACKGROUND

The ability to light cure resin based composites based on the position and orientation of the curing light is an important aspect of radiant energy delivery to dental restorations. While many preparations provide excellent clinical access for curing lights, there are hard-to-reach areas of the oral cavity. In some cases, the curing light tip itself is a limiting factor in how close the light can get to the surfaces being light cured and whether or not it has the correct orientation. Poor orientation of the light tip will lead to resin based composites being inadequately light cured. Inadequate resin polymerization has been implicated in adverse effects on the resin's physical properties, reduction in adhesion to the tooth, a negative impact on the biocompatibility of the resin restorations, an increase in marginal deterioration and wear, and an increase in bacterial colonization at the margins of the restorations.

There has been concern based upon research evidence that high-intensity blue light from curing lights can place dental personnel at risk for ocular damage. The most damaging wavelength range for the retina is blue light, near 440 nm, which is the peak wavelength from many LED curing lights. Blue light is transmitted through the ocular media and absorbed by the retina. While high levels of blue light cause immediate and irreversible retinal burning, chronic exposure to low levels of blue light may cause accelerated retinal aging and degeneration. This chronic photochemical injury to the retinal-pigmented epithelium and choroid can accelerate age-related macular degeneration.

What is needed is a protective shield that blocks harmful light such as light in the blue range or UV spectrum used in curing polymeric resins during dental restorations. The protective shield should be easy to use with respect to take it off and on during the dental restorations.

SUMMARY

According to one embodiment, described herein are loupes shields. The shields can be easily attached to the loupes. The loupes shield is composed of a single filter that blocks harmful light. Additionally, the loupes shield includes a connector that permits the loupes shield to be attached to the loupes lens or housing that holds the loupes lens. The loupes shields described are useful in applications where it is desirable to protect the user from being exposed to damaging light. The loupes shields are useful in dental applications such as, for example, dental restorations, where light is required to cure resin based composites applied to a tooth.

It is to be understood that both the foregoing general description and the following detailed description are merely exemplary and are intended to provide an overview or framework to understanding the nature and character of the claims. The accompanying drawings are included to provide a further understanding and are incorporated in and constitute a part of this specification. The drawings illustrate one or more embodiments, and together with the description serve to explain principles and operation of the various embodiments.

BRIEF DESCRIPTION OF THE DRAWINGS

The accompanying drawings are included to provide a further understanding and are incorporated in and constitute a part of this specification. The drawings illustrate one or more embodiments, and together with the description serve to explain principles and operation of the various embodiments.

FIG. 1 shows an exemplary loupes shield described herein.

DETAILED DESCRIPTION

Additional features and advantages will be set forth in the detailed description which follows and will be apparent to those skilled in the art from the description or recognized by practicing as described in the following description together with the claims and appended drawings.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

"Optional" or "optionally" means that the subsequently described event or circumstance can or cannot occur, and that the description includes instances where the event or circumstance occurs and instances where it does not. For example, the connector of the loupes shield described herein may optionally include grooves on the inners surface of the connector, where the grooves may or may not be present.

As used herein, the term "about" is used to provide flexibility to a numerical range endpoint by providing that a given numerical value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1-about 3, from 1 to about 3, from about 1 to 3, etc., as well as 1, 2, 3, 4, and 5, individually. The same principle applies to ranges reciting only one numerical value as a minimum or maximum. The ranges should be interpreted as including endpoints (e.g., when a range of "from about 1 to 3" is recited, the range includes both of the endpoints 1 and 3 as well as the values in between). Furthermore, such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed, that while specific reference to each various individual combination and permutation of these compounds may not be explicitly disclosed, each is specifically contemplated and described herein. For example, if a light absorber is disclosed and discussed and a number of different polymeric carriers are discussed, each and every combination of light absorber and polymeric carrier that is possible is specifically contemplated unless specifically indicated to the contrary. For example, if a class of light absorbers A, B, and C are disclosed, as well as a class of polymeric carriers D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, ad C; D, E, and F; and the example combination A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such composition is specifically contemplated and should be considered disclosed.

Described herein are loupes shields useful in applications where it is desirable to block damaging light when the user is applying or using light. As will be discussed below, the loupes shields described herein are useful in dental applications, where light cure is typically applied during dental restorations. The loupes shields described herein are designed to fit over any loupes, which makes them universal in their use.

In one aspect, the loupes shield comprises
(a) a single light filter comprising a first hinge member and
(b) a connector for securing the light filter to the loupes, wherein the connector comprises and second hinge member for receiving the first hinge member.

The single light filter as referred to herein does not include multiple layers of filters that block or absorb different wavelengths. In one aspect, the single light filter is composed of a single material. For example, the single light filter is composed of a polymer and a light absorber or orange colored plastic which is substantially attenuates light in the blue range or UV spectrum. In another aspect, the single light filter is composed of the material used to produce orange shields that blocks light having a wavelength of about 400 nm to about 560 nm, or about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, or about 560 nm, where any value can be a lower and upper endpoint of a range (e.g., about 420 nm to about 450 nm). In another aspect, the single light filter is composed of an orange filter that can suppress 99.9% of the blue or UV spectrum in order to protect an operator's eyes.

The shape of the single light filter can vary either circular or oval or square or rectangular or trapezoid shape. The surface of single light filter can vary either flat or convex or convex surround by flat surface, the surrounding flat surface may vary from about 0.2 mm to about 2 mm, or about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm where any value can be a lower and upper endpoint of a range (e.g., about 0.4 mm to about 1.8 mm). The dimension of the single light filter can vary. In one aspect, the dimension of the single light filter is equal or greater than the dimension of the loupes lens to ensure the entire loupes is shielded by the single light filter. The thickness of the single light filter can also vary. In one aspect, the single light filter has a thickness of from about 0.5 mm to about 4 mm, or about 0.5 mm, about 1.0 mm, about 1.5 mm, about 2.0 mm, about 2.5 mm, about 3.0 mm, about 3.5 mm, or about 4.0 mm where any value can be a lower and upper endpoint of a range (e.g., about 1.0 mm to about 2.5 mm).

In one aspect, the single light filter is composed entirely of a single material. For example, the single light filter can be molded into a single piece composed of orange plastic material. Here, the single light filter can be molded to include other features such as the first hinge member and other optional components. In this aspect, the single light filter does not require the use of a separate filter holder with hinge member where the filter is a separate component placed and held in the filter holder. Thus, when the single light filter is a single, molded component, it is composed of a single article, which reduces the cost of manufacturing as well as facilitate the use of the loupes shield.

The loupes shield described herein also includes a connector. The connector is designed such that it can be affixed to the loupes lens or the housing that holds the loupes lens. In one aspect, the connector is an open-circle clip (e.g., semicircle) composed of a flexible material or adjustable circular clip. In this aspect, the flexible and or adjustable connector can be positioned around the loupes lens or housing that holds the loupes lens.

In one aspect, the connector is composed entirely of a single material or multiple materials. For example, the connector can be molded into a single or multiple piece composed of flexible polymeric material or metal or rubber or combinations of them. Here, the connector can be molded to include other features such as the second hinge member and other optional components. In this aspect, when the connector is a single, molded component, it is composed of a single article, which reduces the cost of manufacturing as well as facilitate the use of the loupes shield. The cross section of the connector can vary either square or rectangular or trapezoid or circular or oval shape. The thickness of the connector can vary as well.

In certain aspects, the single light filter and connector can be composed of the same material. For example, the single light filter and connector can be composed of the orange shield material as described above. In other aspects, the single light filter and connector can be composed of different materials.

FIG. 1 depicts an exemplary design of the loupes shield design described herein. The loupes shield 101 is composed of the single light filter 102 and connector 103. The single light filter and connector are connected to one another by a hinge 104, where the single light filter 102 has a first hinge member 104a; and the connector 103 has a second hinge member 104b for receiving the first hinge member of the single light filter. The position of the hinge members presents on the single light filter 102 and connector 103 can vary. As depicted in FIG. 1, the hinge members 104 of the single light filter 102 and connector 103 are position such that the single light filter 102 moves outward or sideward from the connector 103. In other aspects, the hinge members 104 of the single light filter 102 and connector 103 are positioned such the single light filter can slide up and away or slide to the side from the connector. In this aspect, the first 104a and second 104b hinge member are perpendicular to the single light filter 102 and connector 103, respectively.

In one aspect, the 104a and 104b hinge members of the single light filter 102 and 103 connector can be designed to snap in place and unsnapped as needed. In other aspects, the first 104a and second 104b hinge members of the single light filter 102 and connector 103 can be secured to one another by a screw or pin. In certain aspect, the single light filter and connector can be separated from one another so that each component can be cleaned as needed.

The single light filter 102 and connector 103 as depicted in FIG. 1 are each composed of a single or multiple molded materials. The single light filter can include optional features. Referring to FIG. 1, the single light filter 102 can include a tab 105 for lifting up or slide the single light filter 102 away or to the side from the connector 103. In this aspect, the tab 105 is composed of the same material as the single light filter (e.g., orange plastic material). The tap 105 can be half circle or half oval or rectangular or rectangular with round edge or square or square round edge or triangular shape. The tap 105 can be positioned at any position on the perimeter of the single light filter 102.

The connector 103 as depicted in FIG. 1 is a semicircular or circular clip, where the semicircular clip is composed of a flexible material such that the clip can be opened and positioned on the loupes lens or housing that holds the loupes lens or the circular clip, can be adjustable with the dimension of the loupes lens. The cross section of the connector can be round, square, rectangle or trapezoid or oval shape. The connector can include optional features. In one aspect, the inner surface 106 of the connector 103 can include grooves or ribs for further securing the connector to the loupe lens or housing that holds the loupes lens. In another aspect, the inner surface 106 of the connector 103 can include a thin rubber grip for further securing the connector to the loupes lens or housing that holds the loupes lens.

The loupes shields described herein are designed to be easily placed on a loupes, where the single light filter can easily be lifted or slid away from the loupes lens. This feature of the loupes shields described herein is important in applications where the user must focus on a particular point where damaging light is applied. In one aspect, the loupes shields are particularly useful in dental applications. For example, the loupes shields are useful in dental restorations, which involves curing resin bases composites using light in the blue range or UV spectrum. The effectiveness of the restoration is dependent upon the degree of curing of the resin based composites. The loupes shields described herein when positioned on the loupes permit the dental personnel to look directly at the point of cure without being exposed to light that can cause ocular damage. Ultimately, the loupes shields described herein enhance dental restorations by improving the cured resins based composites physical properties and adhesion to the tooth.

ASPECTS

Aspect 1. A loupes shield comprising
(a) a single light filter comprising a first hinge member; and
(b) a connector for securing the light filter to the loupe, wherein the connector comprises a second hinge member for receiving the first hinge member.

Aspect 2. The loupes shield of Aspect 1, wherein the light filter blocks light having a wavelength less than 560 nm.

Aspect 3. The loupes shield of Aspects 1 or 2, wherein the light filter blocks light having a wavelength of about 400 nm to about 560 nm.

Aspect 4. The loupes shield in any one of Aspects 1-3, wherein the light filter covers the entire lens of the loupes or slightly greater.

Aspect 5. The loupes shield in any one of Aspects 1-4, wherein the light filter has different shapes. The shapes vary either circular or oval or square or rectangular or trapezoid shape.

Aspect 6. The loupes shield in any one of Aspects 1-5, wherein the light filter has different surface may be flat or convex or convex surround by flat surface, wherein the surrounding flat surface may vary from 0.2-2 mm.

Aspect 7. The loupes shield in any one of Aspects 1-6, wherein the light filter has a thickness of from about 0.5 mm to about 4 mm.

Aspect 8. The loupes shield in any one of Aspects 1-7, wherein the light filter is not secured to the connector by a filter holder.

Aspect 9. The loupes shield in any one of Aspects 1-8, wherein the connector comprises a semicircular or circular clip.

Aspect 10. The loupes shield in any one of Aspects 1-9, wherein the light filter and connector are the same material or different material.

Aspect 11. The loupes shield in any one of Aspects 1-10, wherein the connector comprises different cross sections.

Aspect 12. A method for blocking light during a dental procedure, the method comprising affixing the loupes shield in any one of Aspects 1-11 over the loupes prior to the application of light.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed is:

1. A loupes shield comprising
   (a) a light filter comprising a single molded component with a first hinge member, wherein the molded component and the first hinge member comprises the same material that blocks light having a wavelength less than 560 nm; and
   (b) a connector for securing the light filter to the loupes, wherein the connector comprises a second hinge member for receiving the first hinge member.

2. The loupes shield of claim 1, wherein the light filter blocks light having a wavelength of about 400 nm to about 560 nm.

3. The loupes shield of claim 1, wherein the light filter covers the entire lens of the loupes or slightly greater.

4. The loupes shield of claim 1, wherein the light filter is circular, oval, square, rectangular, or trapezoid shape.

5. The loupes shield of claim 1, wherein the light filter has a thickness of from about 0.5 mm to about 4 mm.

6. The loupes shield of claim 1, wherein the connector comprises a semicircular or circular clip.

7. The loupes shield of claim 1, wherein the light filter and connector are the same material or different material.

8. The loupes shield of claim 1, wherein the connector comprises different cross sections.

9. A method for blocking light during a dental procedure, the method comprising affixing the loupes shield of claim 1 over the loupes prior to the application of light.

\* \* \* \* \*